(12) United States Patent
Gagnon et al.

(10) Patent No.: US 7,835,558 B2
(45) Date of Patent: Nov. 16, 2010

(54) METHOD AND SYSTEM FOR MAKING DENTAL RESTORATIONS

(75) Inventors: Jean Gagnon, Québec (CA); Christian Saindon, Québec (CA)

(73) Assignee: Tekno Replik Inc., Quebec, Quebec (CA)

( * ) Notice: Subject to any disclaimer, the term of this patent is extended or adjusted under 35 U.S.C. 154(b) by 855 days.

(21) Appl. No.: 11/730,681

(22) Filed: Apr. 3, 2007

(65) Prior Publication Data

US 2007/0243503 A1      Oct. 18, 2007

Related U.S. Application Data

(60) Provisional application No. 60/744,158, filed on Apr. 3, 2006.

(51) Int. Cl.
*G06K 9/00* (2006.01)
*A61C 11/00* (2006.01)
*A61C 5/04* (2006.01)

(52) U.S. Cl. .................. 382/128; 433/213; 433/226

(58) Field of Classification Search .............. 382/128, 382/129, 130, 131, 132, 133, 134; 378/38, 378/168, 191; 433/24, 53, 68, 153, 158, 433/161, 162, 213, 223, 226; 607/47; 700/163
See application file for complete search history.

(56) References Cited

U.S. PATENT DOCUMENTS 4,575,805 A     3/1986   Moermann et al.
5,385,471 A     1/1995   Chuen
5,549,476 A  *  8/1996   Stern ........................ 433/223
5,813,859 A     9/1998   Hajjar et al.
6,375,729 B1    4/2002   Brodkin
6,527,550 B1 *  3/2003   Hajjar et al. ................ 433/53
6,641,340 B1   11/2003   Hajjar et al.
6,685,470 B2 *  2/2004   Chishti et al. ............... 433/24
6,835,067 B2   12/2004   Dorfman
2003/0222366 A1 12/2003   Stangel
2004/0245664 A1 12/2004   Panzera (Continued)

FOREIGN PATENT DOCUMENTS

WO          02074183        9/2002

OTHER PUBLICATIONS

McLarent et al., Fabrication of conservative ceramic restorations using copy-milling technology, Special reprint from Quintessence of Dental Technology, 1994, vol. 17.

(Continued)

*Primary Examiner*—Abolfazl Tabatabai
(74) *Attorney, Agent, or Firm*—BCF LLP

(57) ABSTRACT

A model of the dental restoration is shaped in-vivo on the patient by the dentist. The model is then scanned in the dentists office using a 3D optical scanner. A 3D graphic representation of the model is obtained from the scanner using a computer. The computer is used to convert the 3D graphic representation of the model into a milling path for milling the dental restoration in a block of durable dental restoration material having known dimensions. A mill, also present in the dentists office, mills the dental restoration from the block using the milling path while the patient is waiting. The dentist can then take the milled dental restoration and apply it to the patient in the same, single visit.

19 Claims, 5 Drawing Sheets

U.S. PATENT DOCUMENTS

| | | |
|---|---|---|
| 2004/0254667 A1 | 12/2004 | Ganley |
| 2005/0064360 A1 | 3/2005 | Wen et al. |
| 2005/0110177 A1 | 5/2005 | Schulman |
| 2005/0115460 A1 | 6/2005 | Petticrew |
| 2005/0170315 A1 | 8/2005 | Strobel et al. |
| 2005/0186540 A1 | 8/2005 | Taub et al. |

OTHER PUBLICATIONS

Ringer, The essentials for placing indirect composite inlays and onlays, Cosmetic Dentistry, Oral Health, May 2003.

* cited by examiner

METHOD AND SYSTEM FOR MAKING DENTAL RESTORATIONS

CROSS-REFERENCE TO RELATED APPLICATIONS

The present application claims priority of U.S. Provisional Patent Application No. 60/744,158, filed Apr. 3, 2006, by Applicant.

BACKGROUND

Dental restorations are used as permanent implants to fill the damage from dental cavities or from other causes. Commonly used dental restorations include inlays, onlays, dentinal pins and root pins. For example, an inlay is used to fill a tapered recess defined across an upper portion of a tooth. Dental restorations can be made of various durable materials including metals and porcelain and can be molded or machined. The quality of the dental restoration is typically related to its color and its durability.

Known methods and systems for making dental restorations such as inlays and onlays typically involve creating the dental restoration from a model or mold in a remote lab. The patient takes an appointment for a first visit with his dentist during which the dentist takes an impression of the missing dental tissue. In the case of some restorations, the dentist then fills the damaged region with a temporary fill material. In some cases, these manipulations require anesthesia. The patient then returns home with the temporary fill and the impression is sent to a remote lab where the dental restoration is made by a lab technician, using the impression. The dental restoration is then sent to the dentist.

The patient then takes another appointment for a second visit with his dentist. Some temporary fills have been known to fail between the two visits. In the second visit, the dentist can remove the temporary fill and prepare the damaged region of the tooth to receive the dental restoration. In some cases, this requires a second anesthesia. It is often required that the dentist make final adjustments to the dental restoration to adapt the contours of the restoration to the opposite teeth when the jaw is closed. In some cases, due to occurrence of errors stemming from the several manipulations by the dentist and/or by the remote lab technician, the restoration does not fit, and the process has to be repeated.

The known methods and systems described above have been used for years and have provided a certain degree of satisfaction to its users. However, these methods and systems have been known to suffer from several drawbacks, including the discomfort to the patient caused by the presence of two distinct appointments. There thus remained room for improvements.

SUMMARY

In accordance with the present improvements, a model of the dental restoration is shaped in-vivo on the patient by the dentist. The model is then scanned in the dentist's office using a 3D optical scanner. A 3D graphic representation of the model is obtained from the scanner using a computer. The computer is also used to convert the 3D graphic representation of the model into a milling path for milling the dental restoration in a block of durable dental restoration material having known dimensions. A mill, also present in the dentist's office, mills the dental restoration from the block using the milling path while the patient is waiting. The dentist can then take the milled dental restoration and apply it to the patient in a same, single, visit.

In accordance with one aspect, there is provided a method of making a dental restoration comprising: in a dentist's office, shaping a model of the dental restoration by applying a hardening compound in vivo on a tapered recess in a patient's dental tissue, and hardening the compound in situ; removing the model from the patient's mouth; positioning the model between two holding pin members; while the patient is waiting in the dentist's office, obtaining a 3D graphic representation of the positioned model including in sequence effecting a first scanning of the model while rotating the model with the holding pin members around a rotation axis in a first relative orientation, inclining the rotation axis to a second relative orientation, effecting a second scanning of the model while rotating the model with the holding pin members around the rotation axis in the second relative orientation, and assembling data obtained during the first scanning and the second scanning into the 3D graphic representation of the model; selecting a block of durable dental restoration material having a size sufficient to encompass the dental restoration; creating a milling path of the dental restoration for the selected block, based on the 3D graphic representation of the model; positioning the selected block in a mill; and while the patient is still waiting in the dentist's office, milling the positioned block with the mill in accordance with the milling path to obtain the dental restoration.

In accordance with another aspect, there is provided a system for making a dental restoration, the system comprising: an optical scanner having a frame receiving a model holder having two opposite holding pin members jointly rotatable about a common longitudinal rotation axis, at least one of the holding pin members being displaceable along the rotation axis to apply a compressive force with the other pin holding member to a model of the dental restoration when the model is positioned therebetween, an angular orientation sensor capable of monitoring the angular orientation of the holding pin members around the axis, a transversal pivot axis passing through a center point located between the two pin holding members, a photo-emitter and a photo-receptor both being mounted to the frame at fixed distances relative to one another and relative to the center point, the photo-emitter being oriented to reflect light onto the positioned model and the photo-receptor being oriented to receive the reflected light, the rotation axis being inclinable around the pivot axis relatively to the photo-emitter and the photo-receptor; a computer connected to the optical scanner and capable of creating a 3D graphic representation of the model by correlating signals received from the photo-receptor with angular orientation data received from the angular orientation sensor and data concerning the inclination of the rotation axis, given the fixed distances, and capable of creating a dental restoration milling path for a block of given dimensions and given dental restoration material, based on the 3D graphic representation; and a mill connected to the computer and capable of milling the dental restoration from a block positioned therein using the milling path created by the computer.

In accordance with an other aspect, there is provided a method of treating a tapered recess in a patient's dental tissue in a single visit to a dentist's office, the method comprising: during a patient's visit to the dentist's office, shaping a model of the dental restoration by applying a hardening compound in vivo on the tapered recess in the patient's dental tissue, and hardening the compound in situ; removing the model from the patient's mouth; scanning the model in the dentist's office to obtain a 3D graphic representation of the model; in the dentist's office, milling a dental restoration from a block of durable dental restoration material, using a milling path based on the 3D graphic representation of the model; and applying the dental restoration to the tapered recess in the patient's dental tissue during the same patient's visit to the dentist's office.

DESCRIPTION OF THE FIGURES

Further features and advantages will become apparent from the following detailed description, taken in combination with the appended figures, in which.

DETAILED DESCRIPTION

Figure 1:
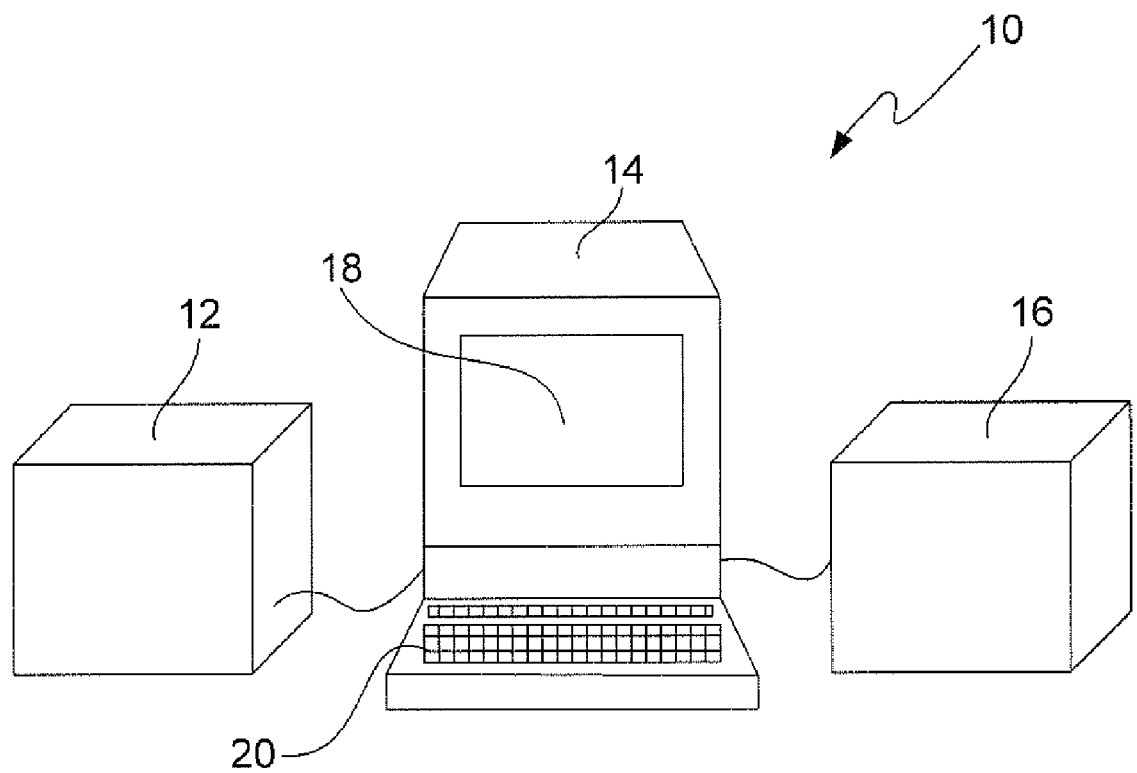
FIG. 1 is a schematic view of an example of an improved system for making a dental restoration.

First, a model of the dental restoration is shaped directly in the client's mouth, then, the model is scanned, and the dental restoration is milled from a bloc based on the model's scan data. All is done in the dentist's office while the patient is waiting. The dental restoration can then be applied to the patient in a single visit. Types of dental restorations which can be made in this manner include dentinal pins, root pins, inlays and onlays.

The present improvements advantageously make use of a model of the restoration shaped directly in the patient's mouth. This helps maintaining a minimal amount of manipulation from the shaping of the model to the milling of the restoration and can reduce the risks of error. Further, by shaping the model directly in the patient's mouth, the dentist can verify that the model does not interfere with other teeth when the jaw of the patient is closed.

The dental tissue to which the dental restoration is to be applied is prepared by defining a tapered recess therewithin. A hardening compound is then applied to the tapered recess in vivo by the dentist, and the compound is hardened.

The model can be made of many types of hardening compounds. One example of such a material is a material which hardens under ultraviolet radiation. Preferably, the hardening material is non-adhesive, in order to be easily removable, and can be removed due to the tapered shape of the recess in the dental tissue. If desired, a layer of adhesion-preventing compound can be applied to the dental tissue prior to application of the hardening compound to prevent adhesion between the hardening compound and the dental tissue.

If shrinkage occurs during hardening, or if a adhesion-preventing compound is used, the resulting model will typically be slightly smaller than the volume of the missing dental tissue. This can be beneficial. Dental restorations typically require application of an adhesive to adhere the dental restoration to the dental tissue. The layer of adhesive has a thickness, and if the dental restoration is of the exact shape and size than the missing dental tissue, the thickness of the adhesive may cause the dental restoration to not properly fit the tapered recess. If just the right amount of shrinkage occurs during hardening, the model may be sized just perfectly to allow for the thickness of the layer of adhesive. The dental restoration can then be made with the exact size and shape than the model and it will be ready to be applied to the patient using a layer of adhesive.

A way of obtaining a model which has the right size to allow for the layer of adhesive when the hardening compound does not shrink during hardening is to apply a layer of a spacing compound having the thickness of a layer of adhesive to the surface of the tapered recess before applying the hardening compound. The resulting model will have the volume of the missing dental tissue minus the thickness of the spacing compound. The spacing compound can advantageously be a non-adhesive compound to help prevent unwanted adhesion between the model and the dental tissue in cases where this can occur.

If the model does not allow a sufficient spacing with the dental tissue for a layer of adhesive, it is also possible to electronically modify the 3D image of the scanned model to offset the surfaces which will be in contact with the dental tissue. The surfaces of the dental restoration or model which are adjacent the dental tissue are referred to herein by the term adhesion surfaces. The dental restoration can then be based on the electronically modified image and be adapted for the layer of adhesive.

Once the model is hardened, it is removed from the patient's mouth. This is possible when the recess in the dental tissue is tapered because the resulting model has a counter-taper shape.

FIG. 1 shows an example of a system 10 which can be used in a dentist's office to scan the model and replicate the 3D image of the model obtained from the scan in a block of durable dental restoration material by milling. The system 10 includes an optical scanner 12, a computer 14, and a mill 16. The computer 14 is connected both to the optical scanner 12 and to the mill 16. The components can be provided in separate rooms or in a same room, in the dentist's office. For instance, the scanner 12 and computer 14 can be provided in the patient's room, and the mill 16 can be placed in another room, to avoid the patient to be encumbered by noise emitted during milling. Alternately, the scanner, computer, and mill can be provided together in a single, stand-alone unit. The computer 14 can have a display 18 to allow visualizing the 3D model obtained by the scanner 12. The computer 14 has a user interface 20 which can be a keyboard, or which can alternately be a touch screen. It is preferred that the user interface 20 be as simple as possible to render the system 10 as easy as possible to use.

In an exemplary mode of operation, the display 18 can indicate to place the model in the scanner 12. When the computer 14 detects that the model is positioned in the scanner 12, the display 18 can request an input from the user to start the replicating process. The user can respond using the user interface 20, and the computer can command the scanner 12 to start scanning the model. The computer 14 can be connected to the mill 16 by a TCP-IP Ethernet connection, for example.

Once the model is scanned, a 3D graphic representation of the model is obtained. The 3D graphic representation of the model can be displayed on the display 18. The user can use the user interface 20 to interact with the computer 14. Using the 3D graphic representation, the computer 14 can propose a block of the durable dental restoration material having a sufficient size for the dental restoration to be milled in it. Three or four distinct sizes of blocks can be used, for example, and the computer 14 can propose to select one of these distinct sizes. The proposed block is indicated on the display 18. The user can then select the proposed size of block and place it in the mill 16. The computer 14 creates a milling path based on the 3D graphic representation of the model, knowing the size of the block. The milling path is communicated to the mill, and the mill can then mill the dental restoration from the block. Once the milling of the dental restoration is finished the dental restoration can be applied to the patient which has been waiting. The patient can thus go home with his dental restoration and does not need to come again for another visit.

Figure 2:
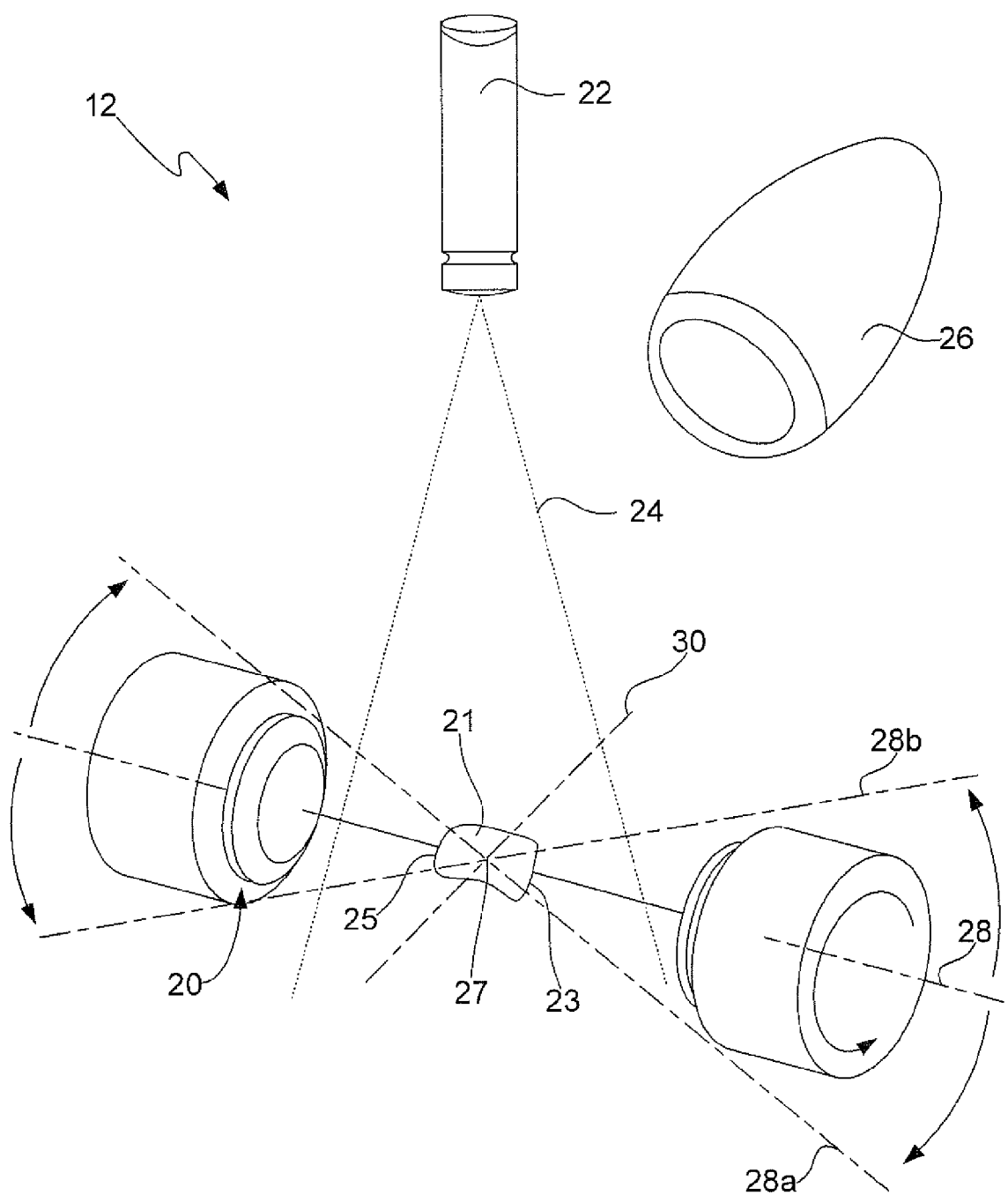
FIG. 2 is a schematic perspective view showing internal components of the scanner of FIG. 1.

The scanner 12 is partially schematized in FIG. 2. The scanner 12 allows to reproduce the model in spatial coordinates (X,Y,Z). The scanner 12 includes a model holder 20 in which the model 21 is held. A laser 22 capable of emitting a flat beam 24 is used as a photo-emitter. A CMOS captor 26, or CCD camera, is used as a photo-receptor to detect rays of the laser bean reflected off the model 21 as the model 21 is rotated about a rotation axis 28 on 360° by rotating the model holder 20. The laser 22 is power modulated and provides structured light to the captor 26. The laser 22 and captor 26 are mounted on a common frame (not shown), at a known distance from a center point 27. The model holder 20 is also mounted to the common frame. The captor 26 is angularly offset from the laser beam by 50° to obtain an image of the laser beam transformed by the model 21. The deviation of the laser beam detected by the captor 26 allows to obtain the spatial coordinates of the surface of the model 21. As the model 21 is rotated, the angular position of the model holder 20 is monitored.

By scanning only as described above, some information can be missing due to hidden areas, such as irregularly shaped recesses in the tips 23, 25 of the model 21, for example. More data can be obtained by relatively inclining the rotation axis 28 about a transversal pivot axis 30, thus placing the rotation axis 28 in a second relative orientation 28a. To obtain increased efficiency, the relatively inclined rotation axis 28a can be kept in the plane of the flat beam 24. The relative inclination can be achieved either by changing the inclination of the tool holder 20, or by changing the inclination of the laser 22 and captor 26 assembly, for example. The model 21 can then be scanned again while rotating the model 21 by 360° around the inclined rotation axis 28a to obtain additional information on the shape of the tip 25. Optionally, the rotation axis 28 can be inclined into a third relative orientation 28b to obtain additional information on the tip 23, for example. In some cases, scanning in more supplemental inclinations can be advantageous. In some other cases, scanning only along the second relative orientation 28a and the third relative orientation 28b, such as a +30° and −30° for example, can be satisfactory. The inclination of the second relative orientation 28a can be of up to 90° from the inclination of the third relative orientation 28b, for example. The use of many distinct and various inclinations can be advantageous in certain alternate configurations.

It can be advantageous for the computer to be programmed in order to detect the presence of hidden areas of the model, and to automatically determine an appropriate inclination to view at least one of such hidden areas. This process can be repeated for remaining hidden areas and the model be scanned at different inclinations until there remains no hidden area on the model.

By bringing all the scanning data to a common coordinate system, a 3D graphic representation of the model is obtained. For example, the scanning resolution selected can be of 20 μm for a zone of 40 mm width and 12 mm height. Before use, the scanner can be gauged by scanning a block of known dimensions. In alternate embodiments, the laser can be replaced by an even source of light, and the captor can be replaced by two cameras spaced by a known distance and oriented toward the model area, in a stereo camera scanning approach instead of the laser scanning approach described above.

Figure 3:
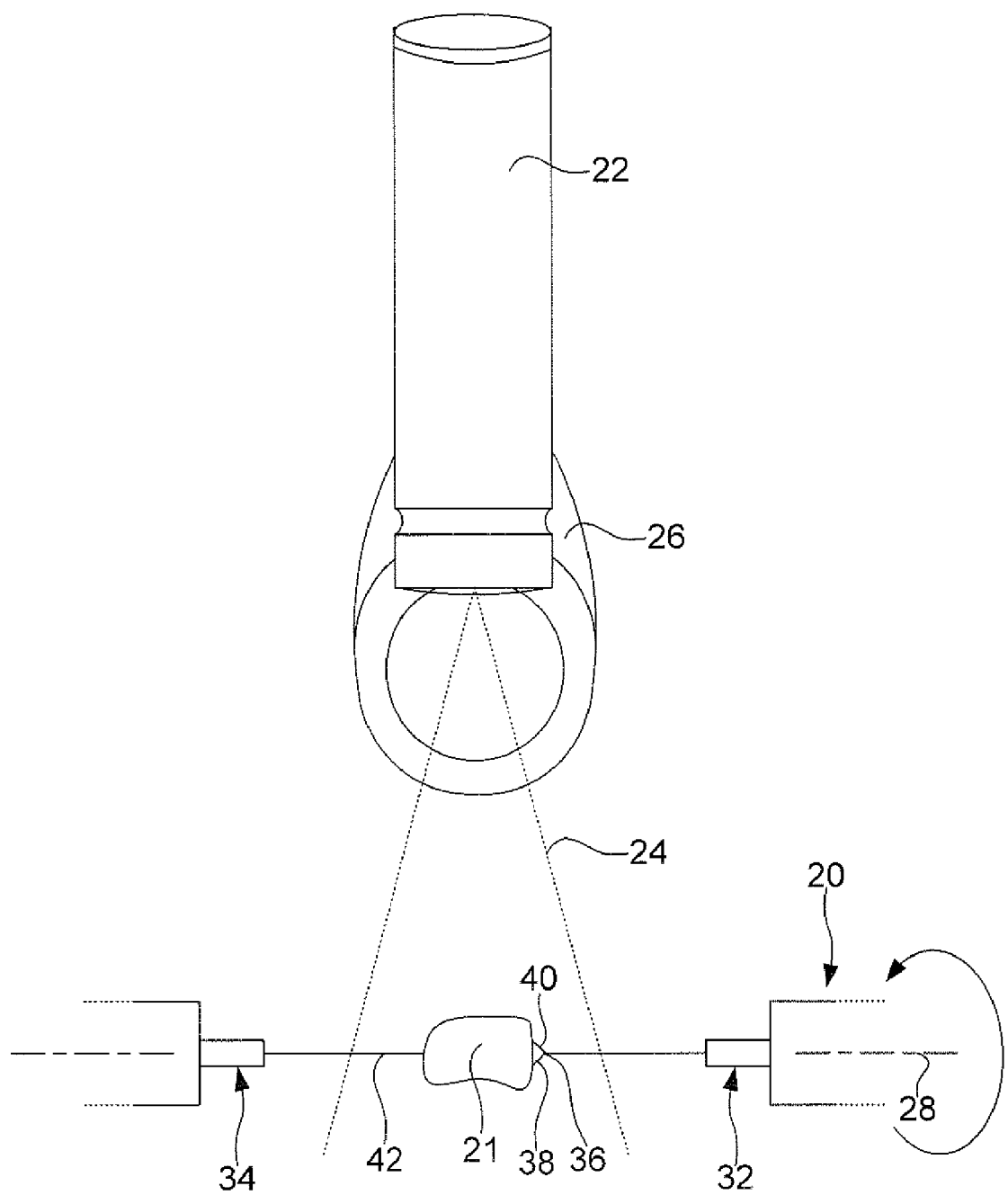
FIG. 3 is schematic front view showing the scanner scanning a model.
Figure 4:
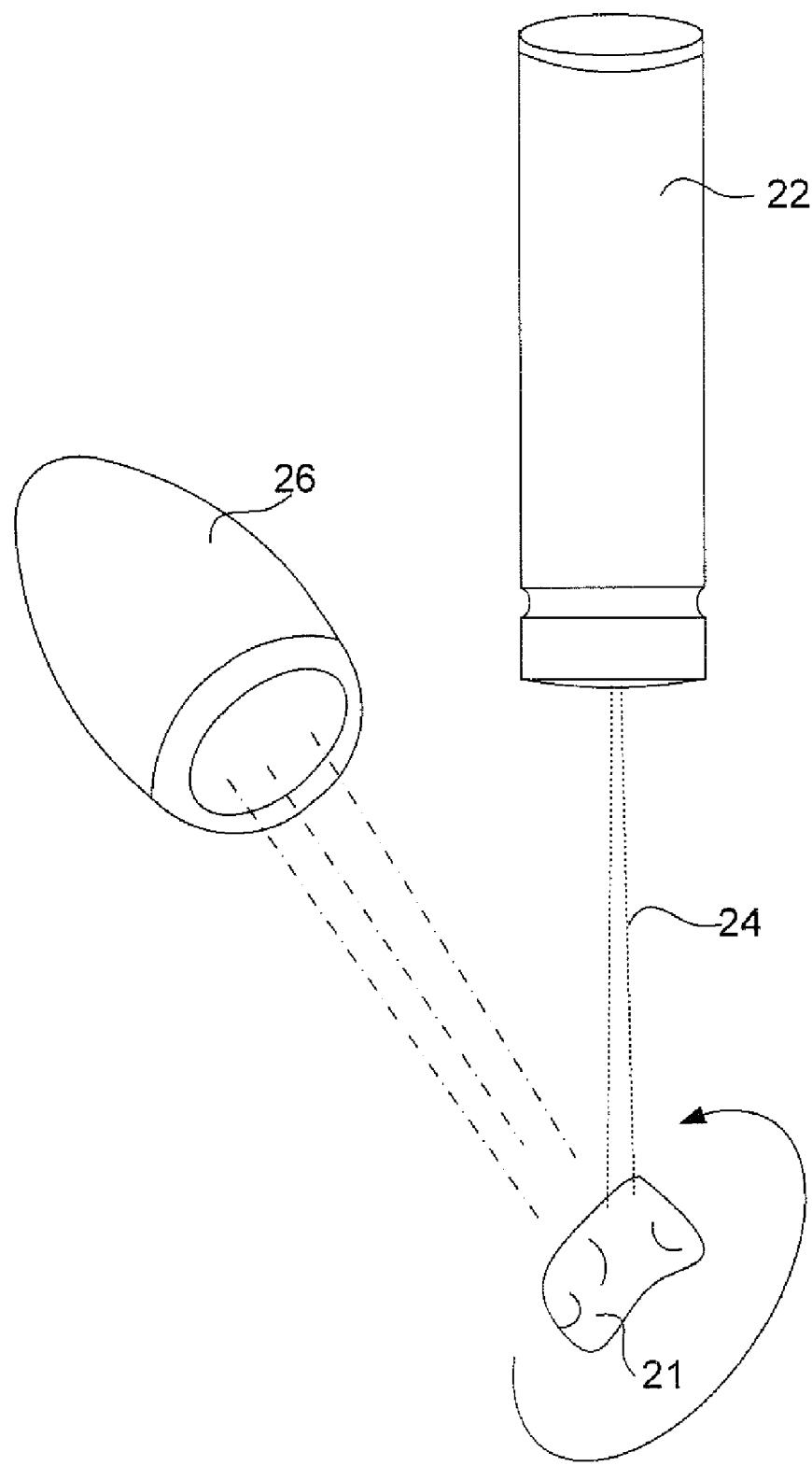
FIG. 4 is a schematic side view showing the scanner scanning a model.

An example of a model holder 20 is shown in greater detail in FIG. 3. The model holder 20 includes a first holding pin member 32 and a second holding pin member 34. The holding pin members use pins, or needles, to hold the model in order to hide as little surface as possible of the model. The first holding pin member 32 is motor-driven for rotation. In this case, the motor is a servo-motor and has an optical encoder which provides angular orientation data to the computer 18. The angular orientation data is used in obtaining the 3D graphic representation.

In this case, the first holding pin member 32 has a Y shaped needle tip 36 including two splayed holding pins 38, 40. The first holding pin member 32 is opposed to a second holding pin member 34. The second holding pin member 34 can be journalled in order to be freely rotatable around the rotation axis 28. The second holding pin member 34 can include a single holding pin 42 at its tip.

One or both holding pin members 32, 34 can be axially displaceable and resiliently biased toward the other holding pin member to allow positioning of the model therebetween and releasing the resiliently biased holding pin member to hold the model. In can be simpler in certain cases that the freely rotatable holding pin member 34 be resiliently biased as compared to the motor driven holding pin member 32. The bias compressive force exerted by the holding pin members on the model 21 can advantageously be selected to allow slight penetration of the holding pins 38, 40, of the first holding pin member 32 into the model 21, to ensure rotation of the model 21 when the motor driven holding pin member 32 is rotated.

To create the milling path using the 3D graphic representation obtained, the following steps can be followed. If modifications are to be made to the 3D graphic representation, to obtain a better fit with the restoration, or to provide a spacing for the layer of adhesive, they can be made electronically. This process can be partially automated, or entirely user decided. The 3D graphic representation of the model then becomes a 3D graphic representation of the dental restoration to be milled. The system can propose a block of sufficient dimensions to contain the dental restoration. The computer is then told which block has been selected. An algorithm can then verify if it is possible to define a milling path based on the desired 3D graphic representation in the selected block. If the verification is negative, the display 18 can indicate to the user to place a larger block in the machine. If this verification is positive, the computer can define the trajectories of the various axes of the mill.

Figure 5:
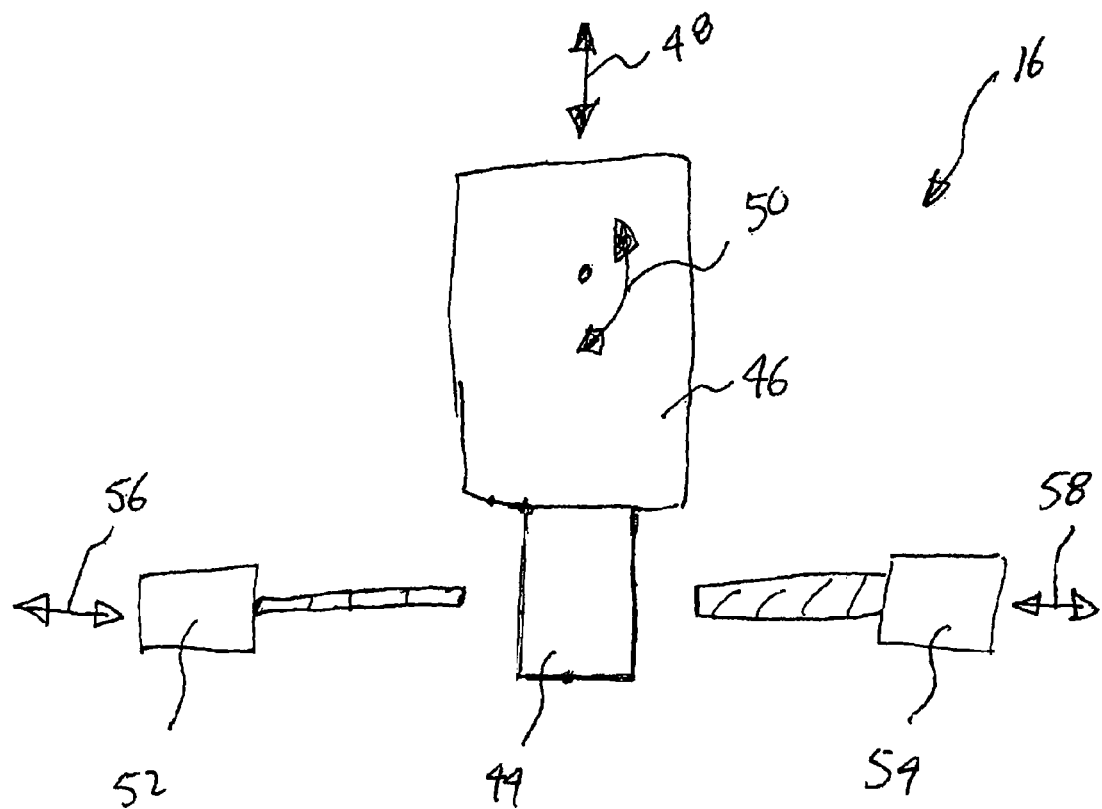
FIG. 5 is a schematic view showing the mill of the system of FIG. 1.

FIG. 5 schematically depicts an example of a mill 16 which can be used. The mill 16 has a controller (not shown) which can operate the mill in accordance with the milling path determined by the computer 14. In this example, the mill has 4 axes. The block 44 to mill is held in a block holder 46. The block holder 46 is axially movable along a first axis 48, and is pivotable along a second, transversal axis 50 to change the angle of the block 44. Two milling tools 52, 54 are used, each milling tool being axially displaceable along a respective axis 56, 58. Because the step of milling is done while the patient is waiting, it is sought to minimize the time it takes to mill the dental restoration out from the block 44. Speed is gained in this case by using two milling tools 52, 54 which work at the same time, but on opposite sides of the block. An algorithm preferably optimizes the positioning of the block to allow efficient access thereto by the milling tools 52, 54.

The block 44 is preferably made of a durable dental restoration material, such as ceramic, gold or titanium. Ceramic is preferred. The type of milling tool used depends on the material of the block 44 used. So does the rotation speed and the feed rate of the tools. Preferably, all the components of the mill are impervious to the cutting fluid used. Impervious and extensible cowls can be used to protect mobile components from cutting fluid incursion.

Gauging of the axes 48, 50, 56, 58 can be realized using a block of known dimensions. In this manner, coordinate systems of the different axes can be combined in a global coordinate system. A gauging procedure can be presented on the display 18 (FIG. 1), to guide the user step-by-step. Maintenance procedures can advantageously be simplified. There are two levels of gauging: correspondence between the axes 48, 50, 56, 58, and adjustment gauging when a milling tool is changed. Correspondence between axes can be done a single time, or periodically, whereas adjustment gauging is done at each time a tool is changed. The computer can be programmed to automatically calculate the lifespan of the milling tools and notify the user when a tool needs to be changed.

The examples described above and illustrated are intended to be exemplary only. The scope of the invention(s) is intended to be determined solely by the appended claims.

What is claimed is:

1. A method of making a dental restoration comprising:
    in a dentist's office, shaping a model of the dental restoration by applying a hardening compound in vivo on a tapered recess in a patient's dental tissue, and hardening the compound in situ,
    removing the model from the patient's mouth,
    positioning the model between two holding pin members,
    while the patient is waiting in the dentist's office, obtaining a 3D graphic representation of the positioned model including in sequence effecting a first scanning of the model while rotating the model with the holding pin members around a rotation axis in a first relative orientation, inclining the rotation axis to a second relative orientation, effecting a second scanning of the model while rotating the model with the holding pin members around the rotation axis in the second relative orientation, and assembling data obtained during the first scanning and the second scanning into the 3D graphic representation of the model,
    selecting a block of durable dental restoration material having a size sufficient to encompass the dental restoration,
    creating a milling path of the dental restoration for the selected block, based on the 3D graphic representation of the model,
    positioning the selected block in a mill, and
    while the patient is still waiting in the dentist's office, milling the positioned block with the mill in accordance with the milling path to obtain the dental restoration.

2. The method of claim 1 wherein obtaining a 3D graphic representation of the model further includes determining the position of at least one hidden area of the model resulting from the first scanning, and determining the second relative orientation based on the position of the at least one hidden area prior to inclining.

3. The method of claim 1 wherein the hardening compound shrinks in a predetermined ratio during hardening and provides a spacing for a layer of dental restoration adhesive between the model and the tapered recess.

4. The method of claim 1 wherein the hardening compound does not shrink during hardening.

5. The method of claim 4 further comprising preparing the tapered recess with a spacing compound having a thickness equivalent to a thickness of a layer of dental restoration adhesive, prior to shaping, and further comprising removing the spacing compound subsequently to removing the model.

6. The method of claim 4 wherein creating the milling path further includes electronically converting the 3D graphic representation of the model into a 3D graphic representation of the dental restoration in which the adhesion surfaces are slightly recessed as compared to the 3D graphic representation of the model to provide a spacing for a layer of dental restoration adhesive between the dental restoration and the tapered recess, and wherein the milling path corresponds to the 3D graphic representation of the dental restoration.

7. The method of claim 1 wherein the first scanning and the second scanning include emitting a flat laser beam across the model as the model is rotated, and receiving a portion of the laser beam having reflected against the model.

8. The method of claim 7 wherein the rotation axis remains within the plane of the flat laser beam during the inclining of the rotation axis.

9. The method of claim 1 wherein obtaining further includes, subsequently to the second scanning, inclining the rotation axis to a third relative orientation, opposite the second relative orientation, and effecting a third scanning of the model while rotating the model with the holding pin members around the rotation axis in the third relative orientation, prior to assembling.

10. The method of claim 1 wherein positioning includes the holding pin members slightly penetrating into the model.

11. A system for making a dental restoration, the system comprising:
    an optical scanner having a frame receiving a pin holder assembly having two opposite holding pin members jointly rotatable about a common longitudinal rotation axis, at least one of the holding pin members being displaceable along the rotation axis to apply a compressive force with the other holding pin member to a model of the dental restoration when the model is positioned therebetween, an angular orientation sensor capable of monitoring the angular orientation of the holding pin members around the axis, a transversal pivot axis passing through a center point located between the two pin holding members, a photo-emitter and a photo-receptor both being mounted to the frame at fixed distances relative to one another and relative to the center point, the photo-emitter being oriented to reflect light onto the positioned model and the photo-receptor being oriented to receive the reflected light, the rotation axis being inclinable around the pivot axis relatively to the photo-emitter and the photo-receptor,
    a computer connected to the optical scanner and capable of creating a 3D graphic representation of the model by correlating signals received from the photo-receptor with angular orientation data received from the angular orientation sensor and data concerning the inclination of the rotation axis, given the fixed distances, and capable of creating a dental restoration milling path for a block of given dimensions and given dental restoration material, based on the 3D graphic representation;
    and a mill connected to the computer and capable of milling the dental restoration from a block positioned therein using the milling path created by the computer.

12. The system of claim 11 wherein a first one of the two opposite holding pin members is motor driven and a second one of the two opposite holding pin members is journalled.

13. The system of claim 12 wherein the first holding pin member has two splayed holding pins extending from a common pin shaft.

14. The system of claim 13 wherein the second holding pin member has a single holding pin.

15. The system of claim 11 wherein the at least one displaceable holding pin member is resiliently biased along the rotation axis toward other holding pin member.

16. The system of claim 11 wherein the photo-emitter is a flat beam emitting laser oriented for the flat beam to extend between the holding pin members, along the rotation axis.

17. The system of claim 16 wherein the pivot axis is normal to the plane of the flat beam.

18. The system of claim 11 wherein the holding pin members are inclinable around the pivot axis relative to the photo-emitter and photo-receptor.

19. The system of claim 11 wherein the computer has a display to show the 3D graphic representation.

\* \* \* \* \*